United States Patent [19]

Hinshaw et al.

[11] Patent Number: 4,794,191

[45] Date of Patent: Dec. 27, 1988

[54] FLUORESCENT CHELATES

[75] Inventors: Jerald C. Hinshaw, Ogden, Utah; John L. Toner, Webster; George A. Reynolds, Rochester, both of N.Y.

[73] Assignee: Eastman Kodak Company, Rochester, N.Y.

[21] Appl. No.: 151,847

[22] Filed: Feb. 3, 1988

Related U.S. Application Data

[60] Division of Ser. No. 7,024, Jan. 27, 1987, which is a division of Ser. No. 825,693, Feb. 3, 1986, Pat. No. 4,637,988, which is a continuation of Ser. No. 279,398, Jul. 1, 1981, abandoned.

[51] Int. Cl.$^4$ ............................................ C07D 311/18
[52] U.S. Cl. ..................................................... 549/211
[58] Field of Search ........................................ 549/211

[56] References Cited

U.S. PATENT DOCUMENTS 4,058,732 11/1977 Wieder ........................... 250/301 X
4,259,313 3/1981 Frank et al. ...................... 424/16 X
4,283,382 8/1981 Frank et al. ...................... 424/16 X
4,352,751 10/1982 Wieder et al. .................. 560/169 X

OTHER PUBLICATIONS

*Chemical Abstracts*, 82:38148K (1975) [Busev et al, *ZH. Anal. Khim.* 1974, 29(8), 1474–7].

*Primary Examiner*—Richard A. Schwartz
*Attorney, Agent, or Firm*—John R. Everett

[57] ABSTRACT

There are described stable fluorescent labels comprising a complex of lanthanide metal and a chelating agent comprising a nucleus which is a triplet sensitizer having a triple energy greater than that of said lanthanide metal and at least two heteroatom-containing groups which form coordinate complexes with lanthanide metals and a third heteroatom-containing group or heteratom in or appended to the triplet sensitizer. Labeled physiologically active materials useful in specific binding assays such as labeled antigens, heptens, antibodies, hormones and the like comprising the stable fluorescent labels having physiologically active materials adsorbed or bonded thereto are also described.

1 Claim, No Drawings

FLUORESCENT CHELATES

CROSS REFERENCE TO RELATED APPLICATIONS

The present application is a divisional of U.S. Ser. No. 007,024 filed Jan. 27, 1987, which in turn is a divisional of U.S. Ser. No. 825,293 filed Feb. 3, 1986, now U.S. Pat. No. 4,637,988 which in turn was a continuation of U.S. Ser. No. 279,398 filed July 1, 1981, now abandoned.

Field of the Invention

The present invention relates to novel fluorescent labels and more particularly to fluorescent labels useful for the preparation of specific binding reagents comprising fluorescent labeled physiologically active materials.

Background of the Invention

In specific binding assays, sensitivity is of prime importance due to the generally low analyte levels that are measured. Radioimmunoassay sensitivity limits the assay to measurements of concentration of $10^{-12}$ M, and more often only in the $10^{-8}$ to $10^{-10}$ M range. In addition, radiolabels suffer from the drawbacks of short half life and handling hazards.

In fluorescence spectroscopy assays, a sample containing a fluorescent species to be analyzed is irradiated with light of known spectral distribution within the excitation spectrum of the target fluorescent species. The intensity of the resulting characteristic emission spectrum of the fluorescent target molecules is determined and is related to the number of target molecules.

The sensitivity of fluorescence assays, although theoretically very high, is limited by the presence of background fluorescence. Background signal levels are picked up from competing fluorescent substances, not only in the sample, but also in materials containing the sample. This is an especially serious problem in quantitative measurements of species associated with samples containing low concentrations of desired target fluorescent molecules such as found in biological fluids. In many situations, it is impossible to reduce the background sufficiently (by appropriate filtration and other techniques known in the art) to obtain the desired sensitivity.

Time resolution offers an independent means of isolating the specific fluorescent signal of interest from nonspecific background fluorescence. Time resolution is possible if the label has much longer-lived fluorescence than the background, and if the system is illuminated by an intermittent light source such that the long-lived label is measureable during the dark period subsequent to the decay of the short-lived background. Such techniques are described in greater detail in German Offenlegungsschrift 2,628,158 published Dec. 30, 1976.

The long-lived fluorescence (0.1-5 msec) of the aromatic diketone chelates of certai rare-earth metals, for example, europiumbenzoylacetonate and europiumbenzoyltrifluoracetonate, has been known for some time. The chelating agent absorbs light and transfers it to the metal ion, which fluoresces. German OLS No. 2,628,158 describes the use of time resolution in fluorometric immunoassays (FIA) through the use of fluorescent labels whose emissions are long-lived as compared with those of species which produce background interferences in such assays. This publication also provides a useful discussion of the techniques of FIA and its advantage over other immunoassay techniques such as radioimmunoassay (RIA).

The fluorescent immunoreagents described in German OLS No. 2,628,158 comprise at least one member of the immune system, i.e., an antibody or an antigen, "conjugated" with a rare-earth chelate. Such "conjugation" can be achieved in one of two ways:

(1) first, by labeling, i.e., attaching the rare-earth chelate to the antigen as described in *Fluorescent Antibody Techniques and Their Application* by A. Kawamura, Ed., University Park Press, Baltimore, Md., 1969, and then adding antibody to the conjugated antigen whereby the antibody and antigen join in the usual fashion, or:

(2) by covalent bonding of the antibody to the chelate via a chemical group which binds to both antibodies and the chelates.

The problem with immunoreagents of the type described in German OLS No. 2,628,158 is that the fluorescent labeling species, namely, the rare-earth chelates, are quenched, i.e., their fluorescence is extinguished, when contacted with water. This problem, hereinafter referred to as an "aqueous stability" problem, is particularly serious because a principal use for fluorescent labeled immunoreagents is in the assay of aqueous biological liquids such as blood, serum, etc. If aqueous stability could be conferred on these materials, they would be useful as fluorescent labels for these biological liquids, thus allowing increased fluorescence immunoassay sensitivity by the use of time resolution of signal from background.

Further, rare-earth chelates previously used for fluorometric measurements have had undesirable properties such as a low quantum yield for emission, undesirable sensitizer extinction coefficients which result in insufficient fluorescence using small quantities of detectable species, low $\lambda$max which renders the determination subject to interference from other components in the sample which are usually in the low $\lambda$max range, poor water solubility (most biological fluids are aqueous) and poor stability of the chelate at low concentrations.

SUMMARY OF THE INVENTION

Highly fluorescent compounds have been discovered which are chelates of a lanthanide metal and a chelating agent comprising a nucleus which is a triplet sensitizer having a triplet energy greater than that of the lanthanide metal and at least two heteroatom-containing groups which form chelates (coordinate complexes) with lanthanide metals, add a third heteroatom-containing group or heteroatom which is in the sensitizer or appended to the sensitizer nucleus. The chelates are water-soluble, stable at low concentrations at pH of 8 or 10, highly sensitive, and have favorable molar extinction coefficients (10,000–40,000) and favorable $\lambda$max. Accordingly, the present invention provides a class of highly efficient, aqueous-stabilized fluorescent labels for physiologically active materials such as antigens and hormones. The present invention also provides a new class of specific binding reagents, such as antigens, enzymes, hormones and the like bearing these highly useful fluorescent labels.

The reagents are formed by adsorbing or covalently binding the fluorescent labeled antigens, haptens, antibodies, plant lectins, carbohydrates, hormones, enzymes and oteer such species-specific materials.

DESCRIPTION OF PREFERRED EMBODIMENTS

Generally, any lanthanide metal is useful in the chelates described herein. Examples of lanthanide metals useful herein are europium and terbium and are described by Sinha, S. P., *Complexes of Rare Earths*, Pergamon Press, 1966.

The lanthanide metal is complexed with a chelating agent comprising a nucleus which is a triplet sensitizer having a triplet energy greater than that of the lanthanide metal and at least two heteroatom-containing groups and a third heteroatom-containing group or heteroatom which is in or appended to the triplet sensitizer nucleus, each of said two heteroatom-containing groups appended to different carbon atoms of the triplet sensitizer nucleus, said heteroatom-containing groups forming coordinate complexes with lanthanide metals and said groups being located in said chelating agent such that they and said third heteroatom or heteroatom-containing group are capable of forming a chelate structure with the lanthanide metal.

The nucleus of the chelating agent is any triplet sensitizer having the requisite triplet energy. Examples of triplet sensitizers useful herein include ketones such as benzophenone, propiophenone, Michler's ketone, acetophenone, 1,3,5-triacetylbenzene, isobutyrophenone, 1,3-diphenyl-2-propanone, triphenylmethyl phenyl ketone, 1,2-dibenzoylbenzene, 4,4'-dichlorobenzophenone, 1,4-diacetylbenzene, 9-benzoylfluorene, p-cyanobenzophenone, β-naphthyl phenyl ketone, 2-acetonaphthone, α-naphthyl phenyl ketone and 1-acetonaphthone, including α,β-diketones such as biacetyl, benzil and 2,3-pentanedione; a ketoaromatic compound such as xanthone, thioxanthone, anthraquinone, α-naphthoflavone, flavone, 5,12-naphthacenequinone and fluorenone; an aldehyde such as benzaldehyde, phenylglyoxal, ethyl phenylglyoxalate, 2-naphthaldehyde and 1-naphthaldehye; a linear or fused polycyclic aromatic compound such as fluorene, triphenylene, phenanthrene, naphthalene and pyrene; heterocyclic and aromatic nitrogen-containing compounds such as carbazole, terpyridines, phenanthroline, triphenylamine, thiazolines, especially 2-organocarbonylthiazolines such as 2-benzoylmethylene-1-methylnaphtho[1,2-d]thiazoline, 2-furoylmethylene-1-methylnaphthol[1,2-d]thiazoline, 2-(difuroylmethylene)-1-methylnaphtho[1,2-d]thiazaline, 1-methyl-2-thenoylmethylenenaphtho-[1,2-d]thiazoline and 2-(dithenoylmethylene)-1-methylnaphtho[1,2-d]thiazoline; thiazoline compounds as described in U.S. Pat. Nos. 2,732,301 and 4,119,466; and ketocoumarins such as described in U.S. Pat. No. 4,147,552.

When the lanthanide metal is europium the triplet energy must be at least about 47 Kcal, and if the lanthanide metal is terbium the triplet energy of the nucleus must be at least about 53 Kcal.

The chelating agent also comprises at least two heteroatom-containing groups which are located on the chelating agent such that they are capable of forming coordinate bonds with lanthanide metals. Groups capable of forming coordinate bonds with lanthanide metals include nitrilodiacetate, carboxy, hydroxy, alkoxy, amino, amido, carbonyl and mercapto groups. These groups are appended to the nucleus so as to allow chelation of the groups with the lanthanide metal.

Preferred chelating agents have the structure:

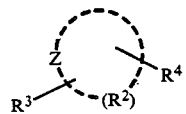

wherein:

Z together with $R^2$ represents the atoms necessary to complete a substituted (such as with a group used to link up the immunoreagent such as ureylene, thioureylene, carbonylimino or imino linked to an immunoreagent, or a coumarin group) or unsubstituted nucleus which is a triplet sensitizer having a triplet energy greater than that of the lanthanide metal;

$R^2$ is selected from the group consisting of a heteroatom and an alkylene group having at least one heteroatom therein or a heteroatom or heteroatom-containing group appended thereto; and $R^3$ and $R^4$ are heteroatom-containing groups which are the same or different which will form a coordinate bond with a lanthanide metal;

$R^3$ and $R^4$ being in sufficient proximity to $R^2$ to allow chelation of the lanthanide metal to $R^2$, and wherein the number of carbon and heteroatoms represented by $R^2$ is equal to or less than 20.

Z together with $R^2$ represents the atoms which complete a substituted or unsubstituted nucleus which is a triplet sensitizer as described hereinbefore.

$R^2$ is a heteroatom such as nitrogen, oxygen, sulfur and selenium or an alkylene group having therein at least one heteroatom or a heteroatom or heteroatom-containing group appended thereto. The number of total atoms represented by $R^2$ is equal to or less than 20. Thus, $R^2$ can comprise one or more heteroatoms. Examples of $R^2$ are —NH—, O, S, Se, —N=,

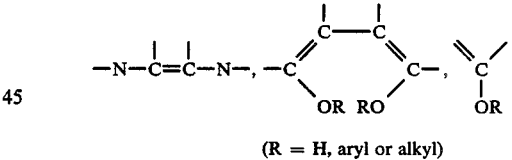

(R = H, aryl or alkyl)

and a heteroatom or a heteroatom-containing alkylene group of up to 10 carbon atoms. Further examples are carbonyl, dicarbonyl, thiocarbonyl, hydroxymethylene, 1,2-dihydroxyethylene and 1,2-dihydroxyvinylene.

$R^3$ and $R^4$ are independently heteroatom-containing groups such as described hereinabove and are located in sufficient proximity to $R^2$ so that the lanthanide metal chelates with $R^2$. It is preferred that $R^3$ and $R^4$ be either individually adjacent to $R^2$, or three or less atoms removed from $R^2$.

In one preferred embodiment, the lanthanide metal is chelated with a phenol having iminodiacetate groups substituted in each position ortho to the phenolic hydroxy group. The phenol is unsubstituted or substituted with a variety of groups such as alkoxy, alkyl, halogen and carbonyl and is optionally fused to another aromatic group or to an alicyclic or heterocyclic group. Especially preferred are compounds having the structure:

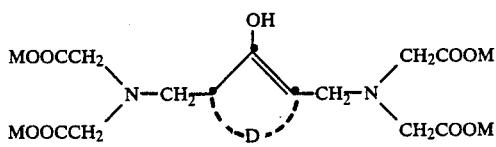

wherein:

M is hydrogen or a cation such as ammonium or its derivatives such as tetramethylammonium, tetraethylammonium and benzyltrimethylammonium or alkali metal such as sodium, lithium, potassium, rubidium and cesium, and D represents the atoms necessary to complete an aromatic ring. This aromatic ring must bear a hydroxyl group as shown above. In addition, it must bear a carbonyl group such as

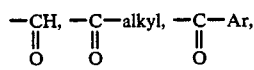

where alkyl generally contains up to about 10 carbon atoms such as methyl and ethyl and Ar is aryl such as phenyl; or it must be fused at two of its available positions to another aromatic, alicyclic or heterocyclic ring preferably containing from about 4 to about 7 carbon atoms such as benzene (substituted or unsubstituted), benzophenone and pyran which bears a carbonyl group to form a coumarin nucleus. Examples of the aromatic ring are phenyl, naphthyl and the like and are optionally substituted in any of the available positions with alkyl, preferably containing from about 1 to about 4 carbon atoms such as methyl, ethyl and propyl, hydroxy and aryl such as phenyl; aldehyde groups such as CHO; benzoyl groups such as:

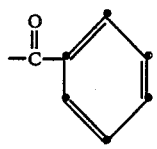

In especially preferred embodiments, D completes a phenyl ring with a carbonyl substituent such as a benzoyl substituent or it completes a coumarin group. Throughout the specification the terms "alkyl" and "aryl" include substituted alkyl and aryl wherein the aryl or alkyl are optionally substituted with groups such as methyl, ethyl and propyl.

A preferred embodiment of the invention involves the formation of a chelate of a lanthanide metal with a salt or acid havng the following structure:

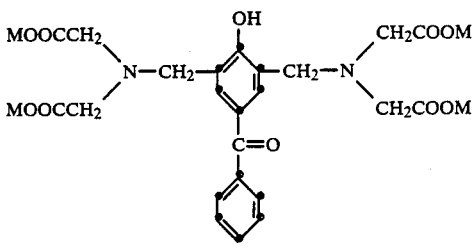

wherein: M is hydrogen, ammonium or an alkali metal ion, or any other suitable cation which renders the salt water-soluble.

In another preferred embodiment, the organic compound which complexed with the lanthanide metal has the following structure:

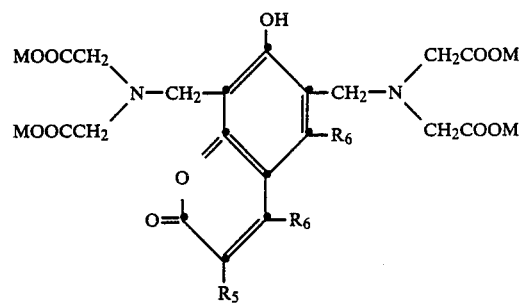

wherein: $R_5$ is preferably aroyl such as:

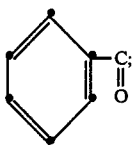

and each $R_6$ is independently hydrogen or alkyl having from about 1 to about 4 carbon atoms such as methyl, ethyl, propyl; aryl or aroyl with or without further substitution; alkoxy such as methoxy and propoxy; or halogen such as bromine or chlorine.

The preferred aroyl $R_5$ substituent is optionally further substituted with aryl or alkyl groups, or with ester, amide, carbamide, thiocarbamide, isocyanate, thiocyanate, halogen or nitrile groups.

Certain other coumarin compounds in which $R_5$ is appended to the coumarin ring by other than an electronegative (i.e., an electron-withdrawing) group are known to fluoresce intensely and are not as useful in the practice of this invention, as this fluorescence prevents the transfer of energy of excitation to the europium or terbium complex with subsequent fluorescence in the visible portion of the spectrum. The organic salt or acid used to form the rare-earth chelate must absorb in the region of 300–500 nm and must then transfer its excitation energy to the lanthanide metal which then fluoresces in the visible portion of the spectrum. Other examples of useful complexing compounds include:

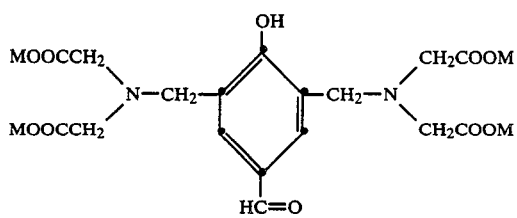

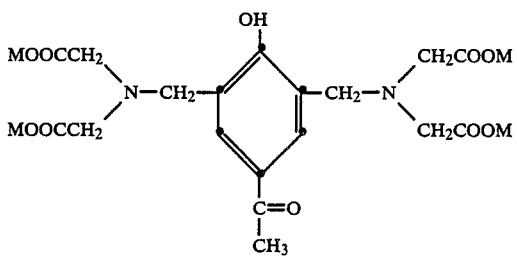

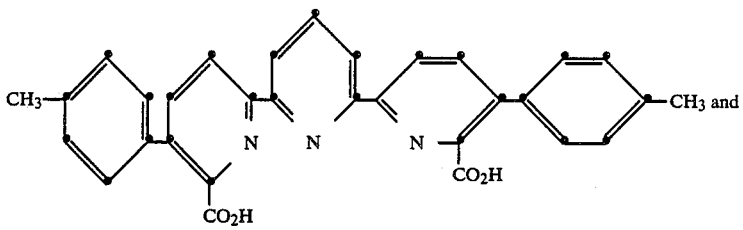

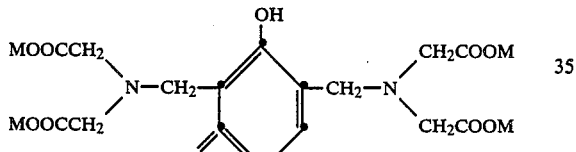

The complex contains any ratio of lanthanide metal to chelating agent. In preferred embodiments, the mole ratio of lanthanide metal to chelating agent is from about 1:1 to about 2:1.

Preferred complexes have a mole ratio of 1:1.

The chelating agents are prepared by performing a Mannich reaction between known compounds of the structure

and iminodiacetic acid or esters thereof, and formaldehyde; or by a nucleophilic displacement reaction between compounds of the structure

which have active methylene groups such as bromomethyl or methylenetosylate groups, and iminodiacetic esters, and in a subsequent step, hydrolyzing the esters.

Useful complexes include

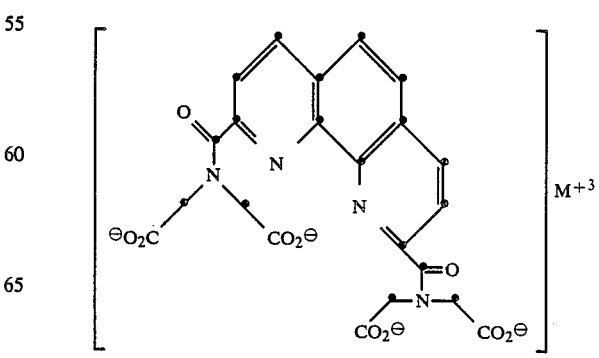

-continued

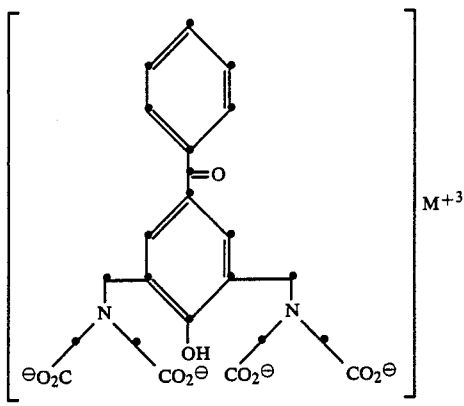

and

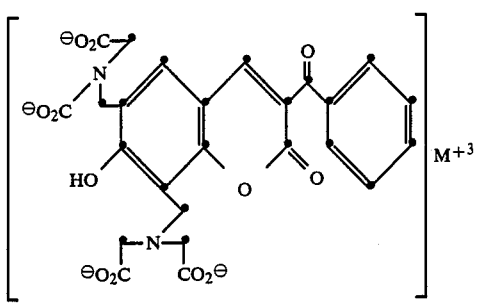

The lanthanide metal and the chelating agent are easily complexed by merely mixing an aqueous solution of the chelating agent with a lanthanide metal salt in an aqueous solution of pH 7.5-10. The lanthanide metal salt is any water-soluble salt of the metal such as chloride salts such as $TbCl_3 \cdot 6H_2O$; $EuCl_3 \cdot 6H_2O$.

The chelate is genrally prepared in aqueous solution at a pH of between 8 and 11 and preferably 8 and 9.

The chelate optionally is mixed with buffers such as phosphate and borate to produce the optimum pH.

The chelate is useful to label a variety of physiologically active materials by binding said materials to the complex by adsorption or by covalent bonding. Among the physiologically active materials which are labeled in this fashion are enzymes and their substrates, antigens, i.e., any substance which is capable, under appropriate conditions, of reacting specifically in some detectable manner with an antibody, carbohydrate, metabolites, drugs, other pharmacalogical agents and their receptors and other binding substances. Specific binding assay reagents are described in U.S. Pat. Nos. 3,557,555, 3,853,987, 4,108,972 and 4,205,058.

Techniques for performing such binding of physiologically active materials to the complexes are those wellknown in the art and include simply mixing the materials together.

In specific binding assay methods, a compound having structural similarity to the analyte being determined is bonded to a detectable label. The analyte being determined is herein referred to as the ligand and the labeled compound as the ligand analog. Compounds which specifically recognize the ligands and ligand analogs and bond to them are referred to as receptors.

In performing one such type of assay, the ligand is placed in competition with the ligand analog for binding to the receptor. Unknown concentrations of the ligand are inferred from the measured signal of the labeled, ligand analog. The reaction proceeds as follows:

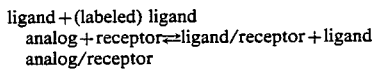

For illustrative purposes, the discussion which follows describes one particular type of specific binding assay technique, a competitive binding fluorescence imunoassay technique.

This system consists of antigen labeled with a fluorescent label of the present invention, unlabeled native antigen (in test sample) and specific antibody whereby there is competition between the unlabeled antigen and the labeled antigen for binding to the antibody. The greater the concentration of unlabeled antigen from the test sample in the system, the less the labeled antigen will be bound by the antibody. If the concentration of labeled antigen and antibody is fixed and the only variable is the level of unlabeled antigen, it is possible to determine the unknown level of unlabeled antigen by physically separating the antigen-antibody complex from the remaining free antigen (both labeled and unlabeled) and comparing the fluorescence of the labeled antigen, either free or bound, with a standard curve plotting of the values given by a range of known amounts of the antigen treated in the same manner.

A preferred fluorescently labeled specific binding reagent comprises a complex of a lanthanide metal and a chelating agent having the structure:

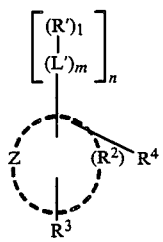

wherein: Z, $R^2$, $R^3$ and $R^4$ are as described above and L' is a linking group such as an ester such as

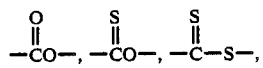

amide such as

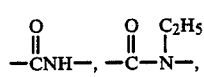

sulfonamide such as $SO_2NH-$,

ether such as $-O-$, $-S-$, carbonyl such as

nitrilo such as =N—, and imino such as —NH—, including those groups comprising additional organic linking atoms such as arylene and thioarylene;

l and m are 0 or 1, n is 1 to 3, and R' is a physiologically active material such as an antigen or hormone.

Once prepared as described hereinabove, the fluorescent-labeled, physiologically active species is useful in fluorescent specific binding assays, particularly those which utilize temporal resolution of the specific detecting signal to distinguish from background as described in aforementioned German OLS No. 2,628,158. In this time-resolved mode (i.e., temporal resolution), the sample is excited in an intermittent fashion and information is accepted only duiing the dark cycle when the long-lived fluorescent label is still emitting strongly but when other sources of fluorescence have decayed. Discontinuous excitation is achieved in a variety of ways, including pulsed laser, mechanical chopping of a continuous excitation beam and moving the sample in and out of the excitation beam. Moreover, discontinuous excitation has the advantage of allowing the use of high radiant power without the absorption of a large amount of energy by the sample, thus diminishing the probability of sample photodegradation.

Examples of such fluorescent specific binding assay techniques wherein the specific binding reagent described herein find utility are described in U.S. Pat. Nos.3,998,943, 4,020,151, 3,939,350,44,220,450 and 3,901,654.

In a preferred embodiment, the specific binding assay is carried out in a dry analytical element such as described in copending U.S. application Ser. No. 973,669 filed Dec. 27, 1978, by Pierce and Frank. In this embodiment, the element contains a support and a spreading/reagent layer comprised of polymeric beads, and optionally a registration layer. In some cases, the spreading layer is separate from the reagent layer. The spreading, reagent and registration layers optionally comprise the polymeric bead structure. The polymeric beads of the reagent layer have receptors such as antibodies adsorbed to their surfaces.

The chelate label of the present invention is placed above, below, or in the reagent layer in a manner that prevents the specific reaction from occurring prior to sample wetting, or it is spotted onto the element concurrently with or subsequent to the sample. It is only necessary that the labeled ligand analog permeate the element upon wetting subsequently to compete with the unknown amount of ligand in the sample in the formation of the ligand-receptor complex. The assay is performed by fluorimetrically determining the amount of free labeled ligand analog present or the amount of bound labeled ligand analog-receptor complex.

The following nonlimiting examples will serve better to illustrate the successful practice of the instant invention.

EXAMPLE 1

A complex was formed by mixing equimolar amounts of $TbCl_3.6H_2O$ in an aqueous solution containing a borate buffer which results in a pH of 9 with a compound having the structure:

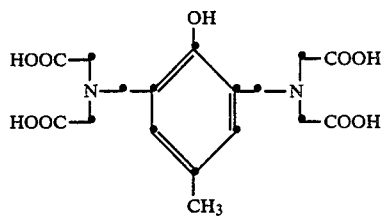

which was prepared by the method described by G. Schwarzenbach et al, *Helv. Chim. Acta,* 35, 1785 (1952). A bright green emission was shown when the solution was excited with a long-wavelength UV lamp (Model UVL-21 Blak Ray ® lamp having a λmax at 366 nm).

EXAMPLE 2

To a stirred solution of 9.9 g (.05 mole) of p-hydroxybenzophenone and 13.7 g (0.1 mole) of iminodiacetic acid in 60 ml of water containing 9 g of sodium hydroxide were added slowly 8.9 g of 37% aqueous formaldehyde solution. The mixture was stirred and refluxed 5 hours, then cooled to room temperature and brought to pH 2 with 2N hydrochloric acid. The solid which formed was collected, washed with water and air-dried. The product was recrystallized from 500 ml of 90 percent ethyl alcohol to give 5.9 g of white-to-pinkish solid in two crops.

Anal. calcd. for $C_{23}H_{24}N_2O_{10}.H_2O$: C, 54.5; H, 5.2; N, 5.5. Found: C, 54.5; H, 4.8; N, 6.1.

UV spectrum (pH 9 borate buffer) λmax 320 nm, $\epsilon 1.6 \times 10^4$.

An exactly equimolar mixture of the above compound and $EuCl_3.6H_2O$ or $TbCl_3.6H_2O$ in pH 9 borate buffer showed a bright red ($Eu^{+3}$) or green ($Tb^{+3}$) fluorescence when excited with a long-wavelength ultraviolet lamp. The emission intensity from the above europium chelate solution was examined as a function of concentration on a Farrand Spectrofluorimeter ® sold by Farrand Instrument Company. The data displayed a linear decrease in the logarithm of the emission as a function of the logarithm of the concentration from $10^{-5}$ to $10^{-9}$M in europium chelate.

EXAMPLE 3

To a solution of 1.64 g (0.02 mole) of 37 percent aqueous formaldehyde in 25 ml of methanol were added 3.22 g (0.02 mole) of dimethyl iminodiacetate. The solution was concentrated under reduced pressure on a rotary evaporator. Methanol (25 ml) was added to the residue and the solution was again concentrated. To the remaining oil were added 2.66 g (0.01 mole) of 3-benzoyl-7-hydroxycoumarin followed by 4 ml of N-methylmorpholine. The mixture was heated with stirring at 115° C. for 3 hr. The mixture was concentrated under reduced pressure on a rotary evaporator. The resulting thick oil was dissolved in a minimum of $CH_2Cl_2$ and applied to a dry column of silica gel. The column was eluted with 1:4 ethyl acetate:$CH_2Cl_2$. The first yellow band of monoadduct was discarded. The second yellow band was collected. Removal of the solvent under reduced pressure gave 1.6 g of the desired product as a yellow oil which could not be induced to crystallize.

To a solution of 1.5 g (0.0027 mole) of the above tetraester in 20 ml of acetic acid was added 0.6 g (0.003 mole) of cupric acetate monohydrate, followed by 10 ml of water. The mixture was stirred and refluxed under nitrogen for 2 hours. The reaction was cooled to room temperature and brought to about pH 2 with hydrochloric acid. With stirring, the mixture was saturated with hydrogen sulfide gas and allowed to stand 15 minutes. The precipitated cupric sulfide was removed by suction filtration through a diatomaceous-earth pad. The clear orange-brown filtrate was concentrated under reduced pressure on a rotary evaporator. The residue was dissolved in hot ethanol containing 25% water, then allowed to cool finally at 5° C. for several hours. The solid was collected, washed with water and dried in vacuo to give 0.3 g of product. UV spectrum (pH 9 borate buffer) λmax 396 nm, ε 27,000.

Analysis calculated for $C_{26}H_{24}N_2O_{12}$: C, 56.1; H, 4.3; N, 5.0. Found: C, 55.6; H, 4.2; N, 4.6.

An exactly equimolar amount of the above compound and $EuCl_3.6H_2O$ in pH 9 borate buffer showed a bright red emission when excited with a long-wavelength ultraviolet lamp.

The emission intensity from the above europium chelate solution was examined as a function of concentration on a Farrand Spectrofluorimeter. The data displayed a decrease in emission as a function of concentration from $10^{-5}$ to $10^{-10}M$ in europium chelate.

λmax emission 593 nm, 614 nm, 652 nm, 701 nm
Emission quantum yield over 560 to 800 nm=4.5%
Emission quantum yield at 614 nm=3.7%

EXAMPLE 4:Preparation of 2,4-dihydroxy-3,5-bis[N,N-di(ethoxycarbonylmethyl)aminomethyl]benzaldehyde

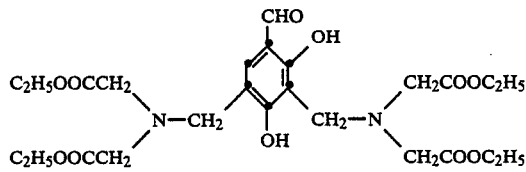

To 8.2 g (0.1 mole) of 37% aqueous formaldehyde in 50 ml of ethanol were added 18.9 g (0.1 mole) of diethyl iminodiacetate. The mixture was concentrated under reduced pressure on a rotary evaporator. An additional 50 ml of ethanol were added and the mixture again concentrated to dryness. To the resulting oil were added 6.9 g (0.05 mole) of solid 2,4-dihydroxybenzaldehyde. The neat mixture was stirred and heated at 120° C. for 3 hours, then used without purification.

The above was repeated using dimethyl iminodiacetate with similar results.

EXAMPLE 5: Preparation of 3-(4-nitrobenzoyl)-7-hydroxy-6,8-bis[N,N-di(carboxymethyl)aminomethyl]coumarin

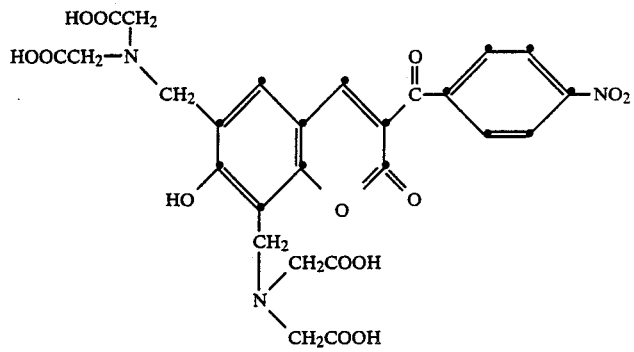

To the above Example 4 crude aldehyde (0.05 mole) were added 11.85 g (0.05 mole) of ethyl 4-nitrobenzoylacetate, followed by 100 ml of ethanol. A solution of 30 mg of acetic acid and 42 mg of piperidine in 1 ml of ethanol was added, and the mixture stirred and refluxed for 16 hours. After this time, the reaction was concentrated on a rotary evaporator. The resulting oil was dissolved in a minimum of $CH_2Cl_2$ and applied to a silica gel dry column. The column was eluted with 150:850 ethyl acetate:$CH_2Cl_2$. The first running colorless impurity and a second running dark-yellow impurity were discarded. The slower-moving light-yellow product band was collected and the solvent removed under reduced pressure. The resulting oil was analyzed by NMR and mass spectroscopy and used directly. Yield, 14.3 g.

To 2.67 g (.00375 mole) of the above tetraester in 75 ml of acetic acid was added 1.0 g (0.005 mole) of cupric acetate monohydrate, followed by 25 ml of water. The mixture was stirred and refluxed under nitrogen for 2 hours. The reaction was cooled to room temperature and brought to about pH 2 with hydrochloric acid. An excess of hydrogen sulfide gas was then passed into the stirred solution, and the mixture was allowed to stand 30 minutes. The precipitated cupric sulfide was removed by suction filtration through a diatomaceous-earth pad. The filtrate was concentrated to dryness under vacuum on a rotary evaporator. The residue was triturated with 50 ml of water. The solid was collected, washed well with water and dried. Yield, 1.2 g. A sample was dissolved in hot 50% aqueous ethanol. The mixture was concentrated under reduced pressure until solid formed. The solid was collected, washed with cold water and dried.

Anal. calcd. for $C_{26}H_{23}N_3O_{14}.H_2O$: C, 50.4; H, 4.1; N, 6.8. Found: C, 50.8; H, 4.1; N, 6.4.

Catalytic reduction of the above chelate in aqueous sodium bicarbonate solution gave the corresponding amino compound.

EXAMPLE 6

A stock solution containing $10^{-4}M$ concentration of a europium chelate described in Example 3 above was diluted with borate buffer (pH 8.5) to concentrations shown in Table I. Ten-microliter aliquots of each concentration were spotted onto analytical elements prepared in the following manner:

A Lexan ® polymer (available from General Electric Company) film support was coated with a microbead layer comprised of poly(styrene-co-methacrylic acid) (weight ratio 98:2) (75.0 g/m²), which had been adsorbed with ovalbumin, carboxymethyl cellulose (0.19 g/m²), Zonyl FSN ® (a nonionic fluorosurfactant obtained from duPont), 0.05% based on total melt weight, normal rabbit serum (0.83 g/m²), poly(n-butyl acrylate-co-styrene-co-2-acrylamido-2-methyl propane sulfonic acid) (weight ratio 70:20:10) (2.25 g/m²) and $H_3BO_3.KCl$ buffer at pH 8.5.

The elements were then evaluated, using a fluorimeter having a Wrattan 18A filter, at Excitation$_{300-400}$ nm and Emmission$_{620}$ nm, at a pH of 8 and a pH of 9.18.

The results shown in the table below illustrate that the fluorescence signal obtained is a function of the concentration of the europium chelate in the sample. The background fluorescence was 50 mV.

TABLE I

| Concentration of Eu Chelate | pH | Fluorescence at Em$_{620}$ nm |
|---|---|---|
| $10^{-8}$ | 8 | 80–100 mV |
| $10^{-7}$ | 8 | 430–450 mV |
| $10^{-6}$ | 8 | 4500 mV |
| $10^{-5}$ | 8 | 40 V |
| $10^{-8}$ | 9.18 | 60 mV |
| $10^{-7}$ | 9.18 | 250 mV |
| $10^{-6}$ | 9.18 | 2.1 V |
| $10^{-5}$ | 9.18 | 20 V |

EXAMPLE 7

A terbium compound prepared as described in Example 3 was tested in the manner of Example 6. The results are shown in Table II with the fluorescence measured at 550 nm and given in µA.

TABLE II

| Concentration of Tb Chelate (M) | pH | Fluorescence at Em$_{550}$ nm (µA) |
|---|---|---|
| $10^{-5}$ | 8.0 | 11.1 |
| $10^{-6}$ | 8.0 | 1.41 |
| $10^{-7}$ | 8.0 | 0.27 |
| $10^{-8}$ | 8.0 | 0.04 |
| $10^{-9}$ | 8.0 | 0.05 |

EXAMPLE 8: Complex of europium and 3,5-bis[N,N-bis(carboxymethyl)aminomethyl]-4'-{N'-[4-(4-hydroxy-3,5-diiodophenoxy)-3,5-diiode-β-methoxycarbonylphenethyl]thioureido}-4-methoxybenzophenone The synthetic scheme for the preparation of the chelating agent is as follows:

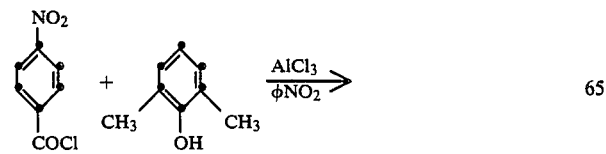

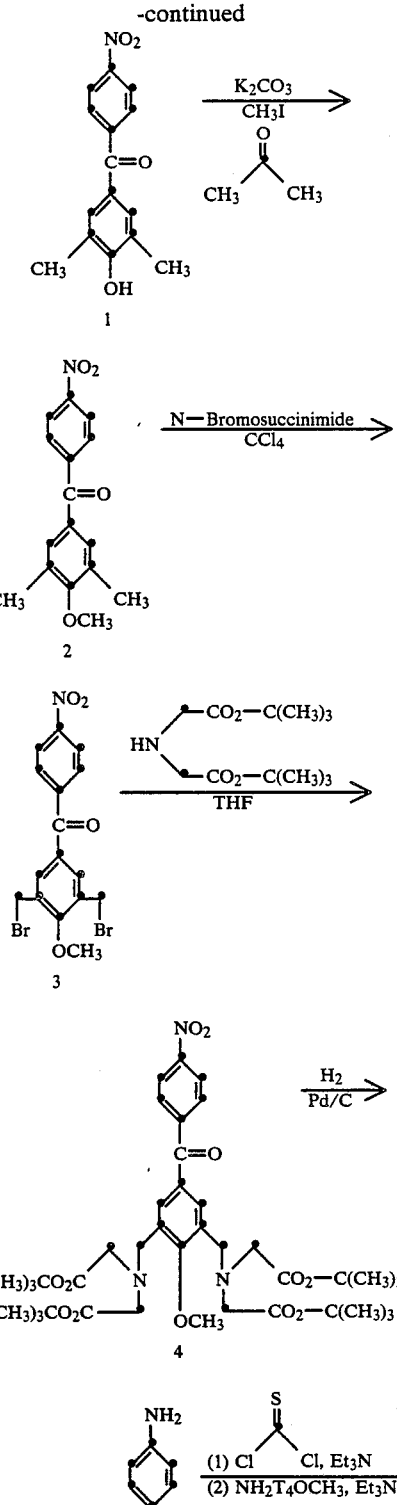

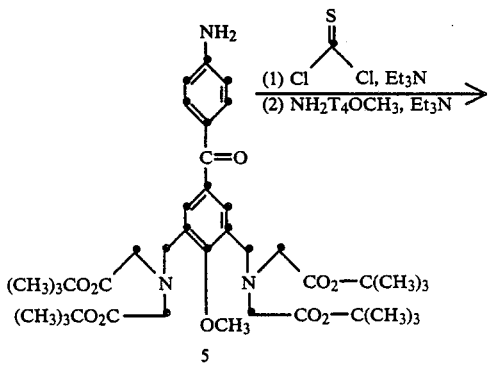

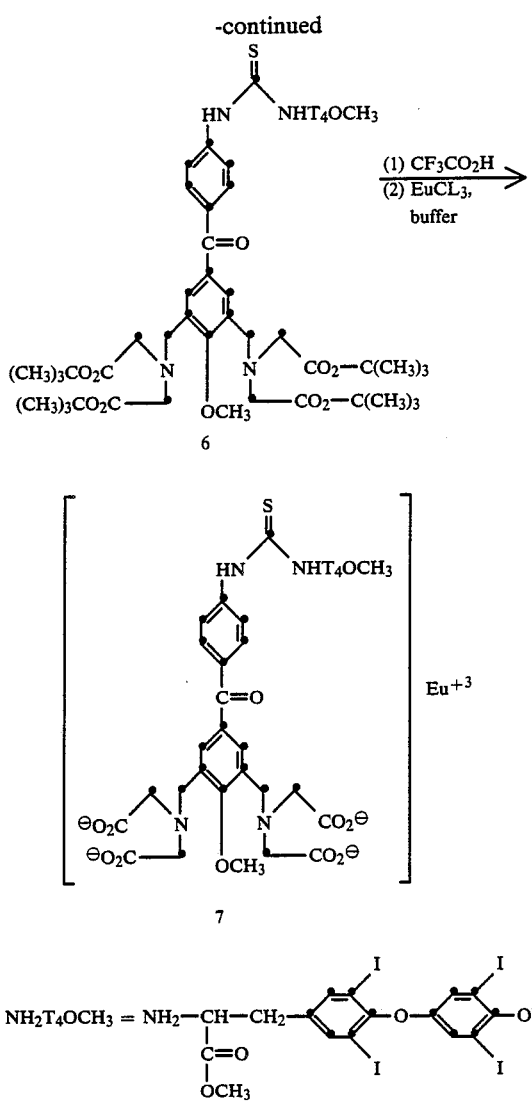

Preparation of 3,5-dimethyl-4-hydroxy-4'-nitrobenzophenone (1)

To a stirring solution of p-nitrobenzoyl chloride (76.1 g, 0.410 mol) in 250 mL nitrobenzene were added 82 g of $AlCl_3$ (0.62mol). To this mixture a solution of 50 grams of 2,6-dimethylphenol (0.41 mole) in 250 mL nitrobenzene was added dropwise over a period of 45 minutes, and the resulting mixture was stirred 16 hours at room temperature. The reaction was poured into 2L of 3% HCl and ice and extracted 3×1L with $Et_2O$ (i.e., three times with 1L each time of diethyl ether). The combined ethereal layers were washed with 1L of saturated $NaHCO_3$, then extracted 2×1L with 10% NaOH. The combined basic extracts were acidified with concentrated HCl to give a white precipitate; filtration followed by recrystallization from $CH_3OH/H_2O$ gave 37 g (33%) of white powder consistent with the desired product by TLC, IR, mass spectroscopy, NMR and elemental analysis, m.p. 182.5–184.5.

Anal. Calcd. for $C_{15}H_{13}NO_4 \cdot H_2O$: C, 62.27; H, 5.24; N, 4.84. Found: C, 62.34; H, 5.31; N, 4.76.

Preparation of 3,5-dimethyl-4-methoxy-4'-nitrobenzophenone (2)

A solution containing compound 1 (15.0 g, 55.4 mmol), $K_2CO_3$ (20.0 g, 0.145 mol) and $CH_3I$ (30 mL, 0.48 mol) in 250 mL acetone was refluxed for 6 hours. The solvent was evaporated and the residue partitioned between $CH_2Cl_2$ and $H_2O$. The organic layer was dried over $Na_2SO_4$, filtered and evaporated to leave a yellow-white powder. Recrystallization from $CH_3OH$/pet ether at $-20°$ C. gave 14.9 g of white crystals (94%) Tee material was characterized by NMR, TLC, mass spectroscopy, IR and elemental analysis, m.p. 131°–132.5° C. Anal. Calcd. for $C_{16}H_{15}NO_4$: C, 67.35; H, 5.31; N, 4.91. Found: C, 67.54; H, 5.38; N, 4.87.

Preparation of 3,5-bisbromomethyl-4-methoxy-4'-nitrobenzophenone (3)

A mixture of compound 2 (4.0 g, 14 mmol) and n-bromosuccinimide (5.0 g, 28 mmol) was refluxed in 250 mL $CCl_4$ with ca. 50 mg dibenzoyl peroxide as a radical initiator for 1 hr under $N_2$. The reaction was cooled to room temperature and 100 mL $CH_2Cl_2$ were added. Filtration followed by extraction of the filtrate with aqueous sodium thiosulfate, drying the organic layer over $Na_2SO_4$, filtration and solvent removal left a white powder. This powder was triturated 3×50 mL with $CH_2CH_2O$ to leave 5.7 g of white powder which contained 3 components by TLC. NMR and mass spectroscopy confirmed the presence of impurities, but the bulk of the material was the desired product.

Preparation of 3,5-bis[N N-bis(t-butoxycarbonylmethyl)aminomethyl]-4-methoxy-4'-nitrobenzophenone (4)

A solution of compound 3 (2.0 g, 4.5 mmol) and di-tert-butyl iminodiacetate (2.2 g, 9.0 mmol) was stirred in 200 mL THF for 60 hr at room temperature. The solvent was removed and the remaining yellow oil was partitioned between $CH_2Cl_2$ and cold aqueous $K_2CO_3$ made from highly purified water. The organic layer was dried over $Na_2SO_4$, filtered and evaporated to leave 4.5 g of yellow oil. A preparative gel permeation column with $CH_2Cl_2$ as the eluent was used to separate the desired product from starting materials and monoadduct. The resulting yellow oil (1.5 g, 43%) could not be induced to crystallize and was characterized by TLC, field desorption mass spectroscopy, NMR and IR.

Preparation of 4'-amino-3,5-bis[N,N-bis(t-butoxycarbonylmethyl)aminomethyl]-4-methoxybenzophenone (5)

Nitrotetraester 4 (3.0 g, 3.9 mmol) was reduced in 50 mL $CH_3OH$ with 100 mg 10% Pd/C in a Parr shaker with an initial hydrogen pressure of 50 psi for 2.5 hours. TLC indicated quantitative reduction. The mixture was filtered through diatomaceous earth and evaporated to leave a yellow oil which was purified by gel permeation chromatography by the method used for compound 4. The yellow glass thus obtained had the correct NMR, IR and field desorption mass spectroscopic behavior.

Preparation of
3,5-bis[N,N-bis-t-butoxycarbonylmethyl)aminomethyl]-
4'-{N'-[4-(4-hydroxy-3,5-diiodophenoxy)-3,5-diiodo-β-
methoxycarbonylphenethyl]thioureido}-4-methox-
ybenzophenone (6)

Tetraester amine 5 (1.7 g, 2.3 mmol) together with triethylamine (1.28 mL, 9.2 mmol) was dissolved in 40 mL dry tetrahydrofuran (THF), followed by the dropwise addition of thiophosgene (0.175 mL, 2.3 mmol) in 10 mL dry THF. The reaction was allowed to proceed for 2 hours, after which the solvent was removed to yield a yellow-orange oil. The oil was dissolved in 60 mL dry N,N-dimethylformamide (DMF) and a solution of L-thyroxine methyl ester hydrochloride (1.9 g, 2.3 mmol) and triethylamine (0.32 mL, 2.3 mmol) in 20 mL DMF was added in one portion The reaction was stirred 1 hour under $N_2$, then poured into 350 mL $H_2O$. Extraction with ether followed by the ether layer being successively washed with three 300-mL portions of purified water, dried over $Na_2SO_4$, filtered and evaportted gave 3.1 g of orange-white foam. This material was purified by gel permeation chromatography to give 1.3 g of the desired product as an orange-white foam. The product was further characterized by TLC, NMR and field desorption mass spectroscopy.

Preparation and evaluation of
3,5-bis[N,N-bis(carboxymethyl)aminomethyl]-4'-{N'-
[4-(4-hydroxy-3,5-diiodophenoxy)-3,5-diiodo-β-
methoxycarbonylphenethyl]thioureido}-4-methox-
ybenzophenone (7)

Tetraester 6 (0.5 g, 0.3 mmol) was dissolved in 15 mL $CF_3CO_2H$ and stirred for 16 hours at room temperature with a drying tube attached to the reaction flask. The solvent wss removed in vacuo to leave an orange foam. Trituration of the foam with $CH_2Cl_2$ produced a yellow-orange powder in quantitative yield. The field desorption mass spectrum shows a parent ion at m/e 1350 and the IR is consistent with the product.

Anal. Calc'd for $C_4H_{38}I_4N_4O_{14}S$: C, 36.5; H, 2.8; N, 4.1; S, 2.4. Found: C, 36.4; H, 2.8; N, 3.7; S, 2.7.

One equivalent of the above compound and two equivalents of $EuCl_3.6H_2O$ in pH 8.5 borate buffer were weakly fluorescent under long-wavelength UV light giving the characteristic red emission. A linear relationship between fluorescence intensity and chelate concentration was demonstrated between $10^{-5}$ and $10^{-7}M$ with the Varian SF330 Spectrofluorimeter® and $\lambda ex=320$ nm, $\lambda em=614$ nm. One equivalent of compound 7 and two equivalents of $TbCl_3.6H_2O$ in pH 8.5 borate buffer were strongly fluorescent under long-wavelength UV light. This chelate also had a linear relationship between fluorescence intensity and chelate concentration between $10^{-5}M$ and $5\times10^{-8}M$.

Cross reactivity is a reflection of how well an antibody recognizes the labeled antigen as compared wit unlabeled antigen. The cross reactivity of the europium chelate of the antigen as determined by known techniques was 75% vs. radiolabeled thyroxine and throxine antibody.

Example 9: Complex of europium with
3,5-bis[N,N-bis(carboxymethyl)aminomethyl]-4-
hydroxy-3'-[4-(4-hydroxy-3,5-diiodophenoxy)-3,5-dii-
odo-β-ethoxycarbonylphenethyl]benzophenone The synthetic scheme for the preparation of the chelating agent of this example is as follows:

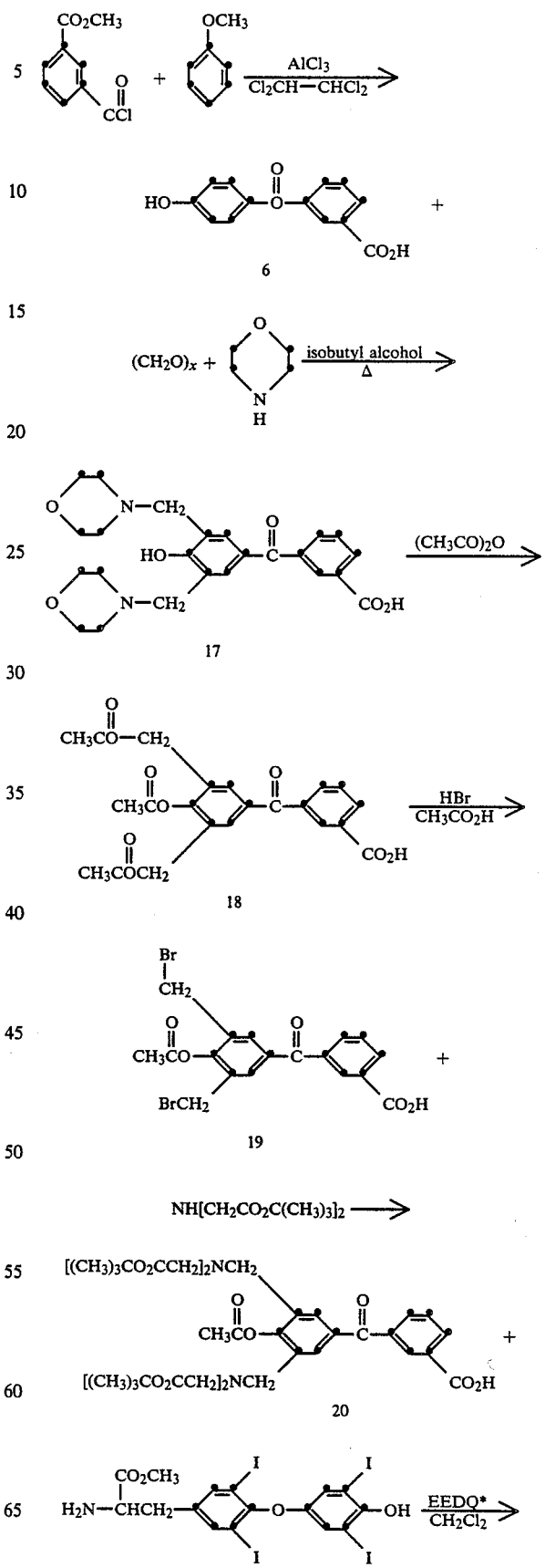

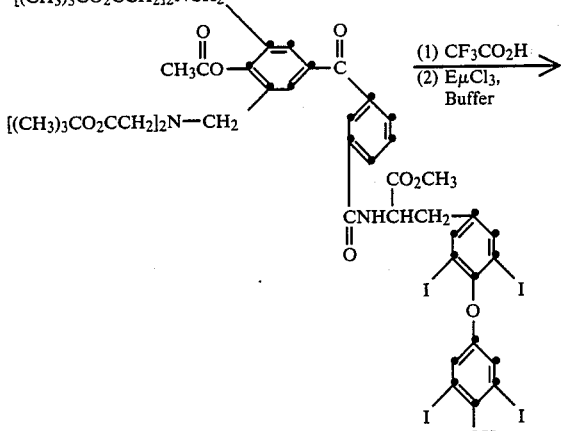

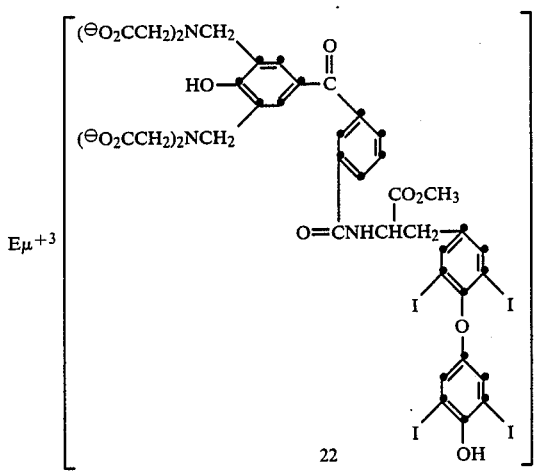

*EEDQ = 1-carbethoxy-1-ethoxy-1,2-dihydroquinoline

3-Carboxy-4'-hydroxybenzophenone (16)

This compound was prepared by the method described in U.S. Pat. No. 3,531,435 (*Chem. Abstracts* 74, 4283V (1971)).

3'-Carboxy-3,5-bis(morpholinomethyl)-4-hydroxybenzophenone (17)

A mixture of 5.22 g (0.06 moles) of morpholine and 1.8 g (0.06 moles) of paraformaldehyde in 50 mL of isobutyl alcohol was refluxed under nitrogen until a clear solution was obtained. To this solution were added 4.8 g (0.02 moles) of 3-carboxy-4'-hydroxybenzophenone (16) and the refluxing was continued for 3 hours. The solution was evaporated under reduced pressure and the gummy residue was stirred several times with ether, giving 9.5 g of solid which was not purified.

4-Acetoxy-3,5-bis(acetoxymethyl)-3'-carboxybenzophenone (18)

A mixture of 9.5 g of 17 and 75 mL of acetic anhydride was refluxed for 24 hours and the excess acetic anhydride was removed under vacuum. The residue was stirred with water and the solid was collected and dried; yield 8.5 g. Thin-layer chromatography (silica gel; 1% methanol in methylene chloride) shows about 10% of the faster moving monoacetoxymethyl derivative is present in the 18.

4-Acetoxy-3,5-bisbromomethyl-3'-carboxybenzophenone (19)

A solution of 2 g of 18, 20 mL of methylene chloride and 5 mL of 31% hydrobromic acid in acetic acid was stirred overnight, 3 mL of acetic anhydride were added and the solution was evaporated to dryness. The residue was chromatographed on silica gel eluting with 1:1 $CH_3CO_2C_2H_5/CH_2Cl_2$ using the method of Still (W. C. Still, M. Kahn and A. Mitra, *J Org Chem*, 43, 2923 (1978)), giving 0.56 g of pure 19 as determined by NMR.

4-Acetoxy-3,5-bis[N,N-bis(t-butoxycarbonylmethyl)aminomethyl]-3'-carboxybenzophenone (20)

A solution of 460 mg (1.07 mmol) of 19, 524 mg (2.14 mmol) of tert-butyl iminodiacetate, and 216 mg (2.14 mmol) of triethylamine in 15 mL of dry tetrahydrofuran was stirred under argon for 2 days. The reaction mixture was filtered to remove triethylamine hydrobromide. The filtrate was evaporated to dryness, giving 900 mg of 20.

4-Acetoxy-3,5-bis[N,N-bis(t-butoxycarbonylmethyl)aminomethyl]-3'-[4-(4-hydroxy-3,5-diiodophenoxy)-3,5-diiodo-β-methoxycarbonylphenethyl]benzophenone (21)

A mixture of 900 mg of 20 and 0.265 g (1.07 mmol) of 1-carbethoxy-2-ethoxy-1,2-dihydroquinoline (EEDQ) in 20 mL of dry tetrahydrofuran was stirred for 30 minutes and 0.85 g (1.07 mmol) of the methyl ester of thyroxine was added. The mixture was stirred overnight. The reaction mixture was purified by gel permeation chromatography using tetrahydrofuran as the solvent, giving 630 mg of material which showed an NRR spectrum which was consistent with structure 21.

3,5-bis[N,N-bis(carboxymethyl)aminomethyl]-4-hydroxy-3'-[4(4-hydroxy-3,5-diiodophenoxy)-3,5-diiodo-β-methoxycarbonylphenethyl]benzophenone (22)

A solution of 630 mg of 21 in 5 mL of trifluoroacetic acid was stirred overnight, diluted with water and the solid which separated was collected and dried; yield 550 mg. The field desorption mass spectrum showed 22 (m/e 1305) is present, as well as some material in which the methyl ester of the thyroxine has been hydrolyzed to the acid.

One equivalent of 22 plus two 2-equivalents of $EuCL_3.6H_2O$ were moderately fluorescent when dissolved in pH 8.5 borate buffer and examined under long-solved wavelength UV light. A linear plot of fluorescence intensity vs chelate concentration was generated between $10^{-5}$ and $10^{-7}M$ for this compound. All fluorescence measurements were taken with a Varian SF330 Spectrofluorimeter ®.

The europium chelate of 22 had a cross reactivity of 80% vs radiolabeled thyroxine and thyroxine antibody.

EXAMPLES 10–16

Europium and terbium complexes with the following chelating agents were prepared as in Example 9 using $EuCl_3.6H_2O$ and $TbCl_3.6H_2O$ in borate buffer:

| Example | Chelating Agent |
|---|---|
| 10 | 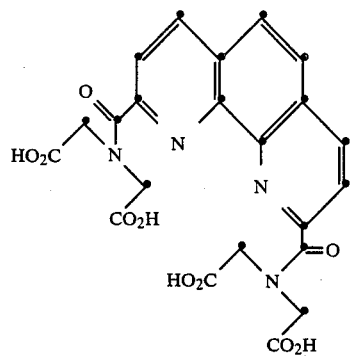 |
| 11 | 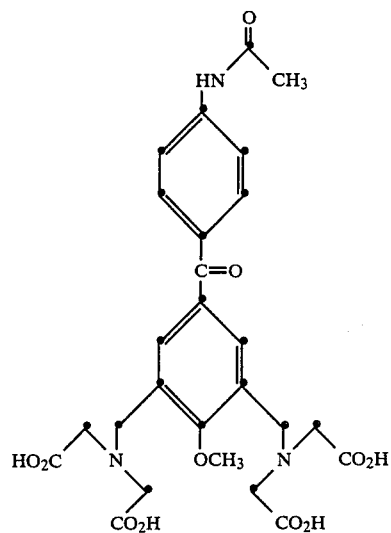 |
| 12 | 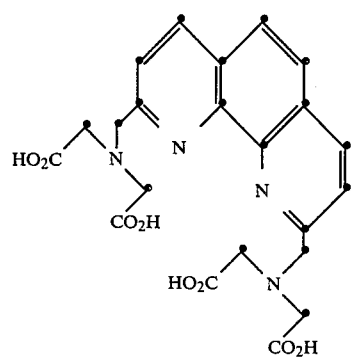 |

-continued
| Example | Chelating Agent |
|---|---|
| 13 | 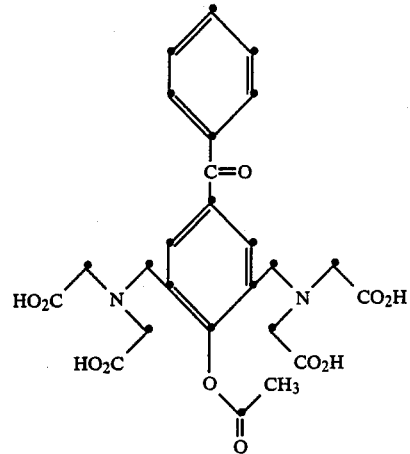 |
| 14 | 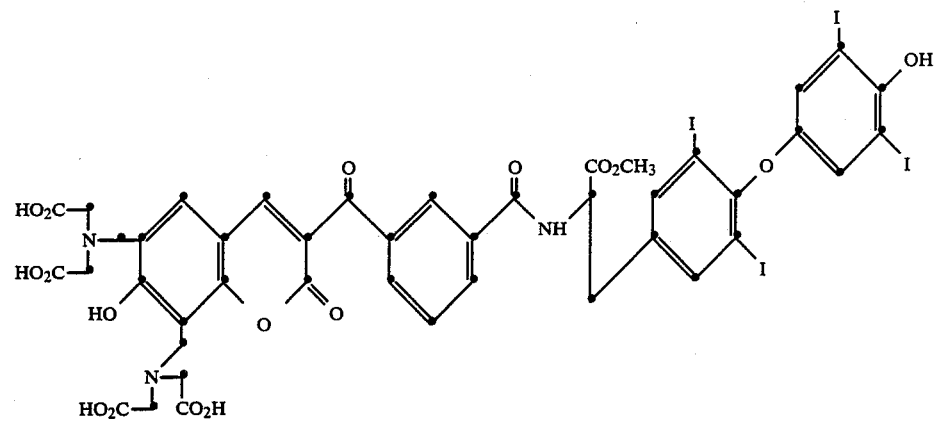 |
| 15 | 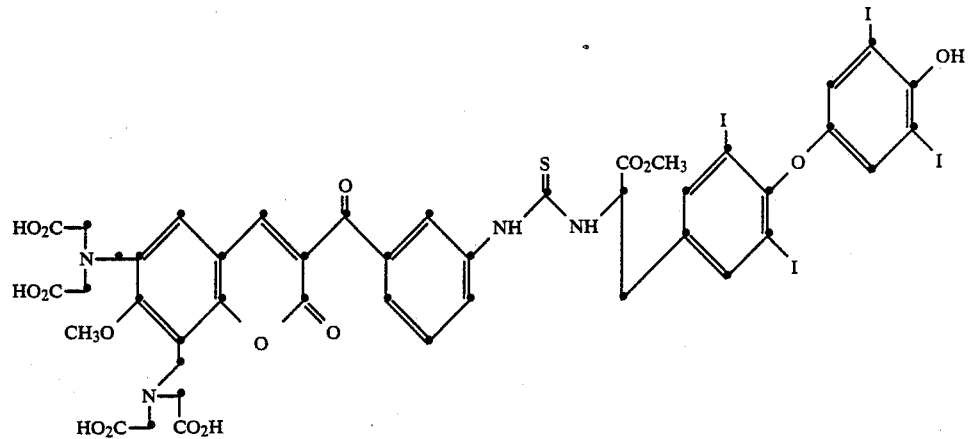 |

| Example | Chelating Agent |
|---|---|
| 16 | 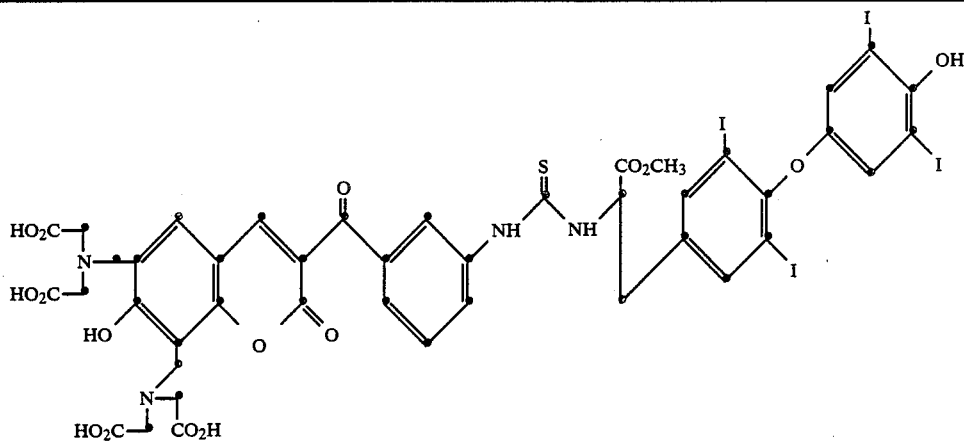 |
| Control A | 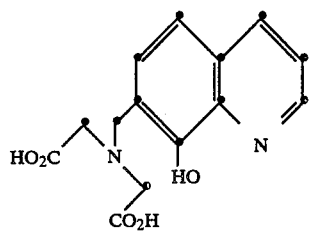 |
| Control B | 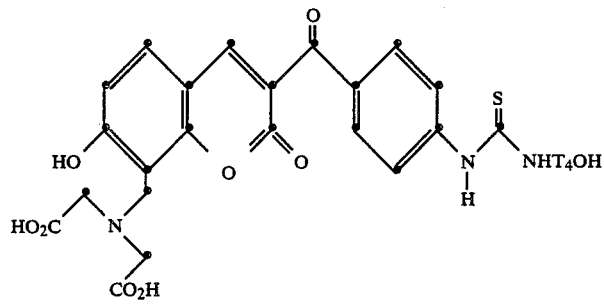 |
| Control C | 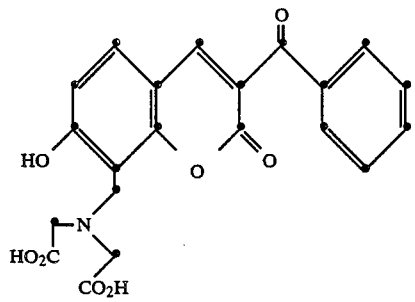 |

The complexes of Examples 10–16 were fluorescent and those of Controls A, B and C were not fluorescent. Complexes of Controls A, B and C were further tested in glycine acetate buffer, phosphate buffer and sodium bicarbonate buffer and were not fluorescent with either $EuCl_3 \cdot 6H_2O$ or $TbCl_3 \cdot 6H_2O$.

The invention has been described in detail with particular reference to certain preferred embodiments thereof, but it will be understood that variations and modifications can be effected within the spirit and scope of the invention.

What is claimed is:

1. A labeled immunoreagent having the structure selected from the group consisting of:

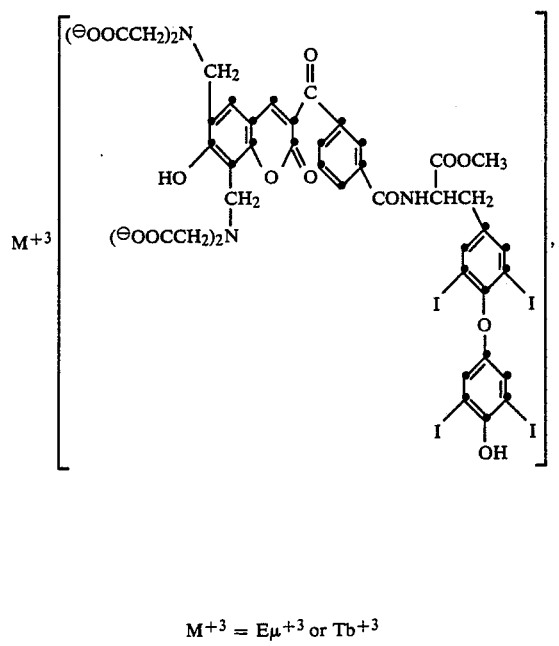
$M^{+3} = Eu^{+3}$ or $Tb^{+3}$
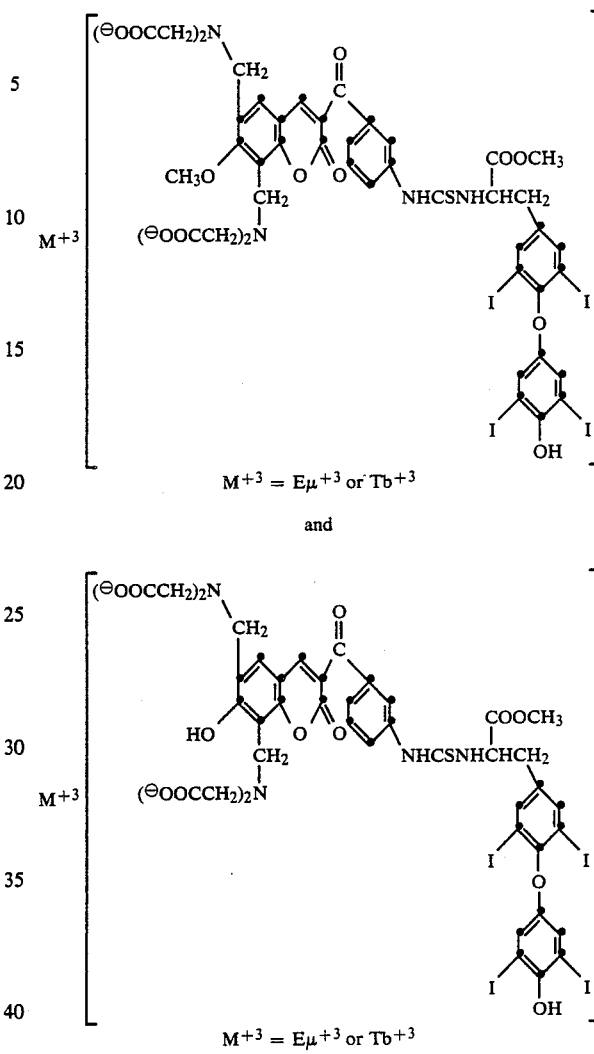
$M^{+3} = Eu^{+3}$ or $Tb^{+3}$
and
$M^{+3} = Eu^{+3}$ or $Tb^{+3}$
* * * * *